United States Patent [19]

Urquhart et al.

[11] Patent Number: 4,479,793
[45] Date of Patent: * Oct. 30, 1984

[54] PARENTERAL ADMINISTRATION USING DRUG DELIVERY DEVICE

[75] Inventors: John Urquhart, Palo Alto; Felix Theeuwes, Los Altos, both of Calif.

[73] Assignee: Alza Corporation, Palo Alto, Calif.

[*] Notice: The portion of the term of this patent subsequent to Jan. 3, 2001 has been disclaimed.

[21] Appl. No.: 540,944

[22] Filed: Oct. 11, 1983

Related U.S. Application Data

[63] Continuation of Ser. No. 325,204, Nov. 27, 1981, Pat. No. 4,424,056.

[51] Int. Cl.³ .............................................. A61M 5/14
[52] U.S. Cl. ........................................ 604/85; 604/251
[58] Field of Search ......................... 604/56, 80-85, 604/251

[56] References Cited

U.S. PATENT DOCUMENTS

| | | | |
|---|---|---|---|
| 1,654,745 | 1/1928 | Miller | 604/83 |
| 2,849,256 | 8/1958 | Kowal | 604/83 |
| 3,305,446 | 2/1967 | Bechtol et al. | 167/72 |
| 3,756,237 | 9/1973 | Chittenden et al. | 128/227 |
| 3,760,984 | 9/1973 | Theeuwes | 222/95 |
| 3,797,494 | 3/1974 | Zaffaroni | 128/268 |
| 3,845,770 | 11/1974 | Theeuwes et al. | 128/260 |
| 3,854,480 | 12/1974 | Zaffaroni | 128/260 |
| 3,921,636 | 11/1975 | Zaffaroni | 128/260 |
| 3,941,126 | 3/1976 | Dietrich et al. | 128/214 |
| 3,948,254 | 4/1976 | Zaffaroni | 128/127 |
| 3,993,066 | 11/1976 | Virag | 128/214 |
| 3,993,072 | 11/1976 | Zaffaroni | 128/260 |
| 3,993,073 | 11/1976 | Zaffaroni | 128/260 |
| 3,995,631 | 12/1976 | Higuchi et al. | 128/260 |
| 4,177,256 | 12/1976 | Michaels et al. | 424/22 |
| 4,203,439 | 5/1980 | Theeuwes | 128/260 |
| 4,217,894 | 8/1980 | Franetzki | 128/213 |
| 4,219,022 | 8/1980 | Genese | 128/214 |
| 4,233,973 | 11/1980 | Shukla | 128/214 |
| 4,256,104 | 3/1981 | Muetterties et al. | 128/214 |
| 4,256,105 | 3/1981 | Leakey | 128/214 |

FOREIGN PATENT DOCUMENTS 49781 11/1970 Switzerland.

OTHER PUBLICATIONS

Surgery, vol. 70, pp. 674–677, 1971.
Brit. J. Anaesth., vol. 43, pp. 681–686, 1971.
Am. J. of I.V. Therapy, pp. 27–30, Dec.-Jan. 1975.
Am. J. Hosp. Pharm., vol. 32, pp. 892–897, 1975.

*Primary Examiner*—Dalton L. Truluck
*Attorney, Agent, or Firm*—Paul L. Sabatine; Edward L. Mandell; Steven F. Stone

[57] ABSTRACT

A parenteral delivery system is disclosed for administering a beneficial agent to a recipient. The system comprises (a) a container of a medical fluid; (b) a primary tubing in communication with the container; (c) a parallel tubing connected to the primary tubing having a formulation chamber connected thereto, the formulation chamber housing a beneficial agent, or a device for delivering a beneficial agent; and (d) a common tubing connected to the primary tubing and the parallel tubing for administering the fluid and the agent to a recipient.

2 Claims, 13 Drawing Figures

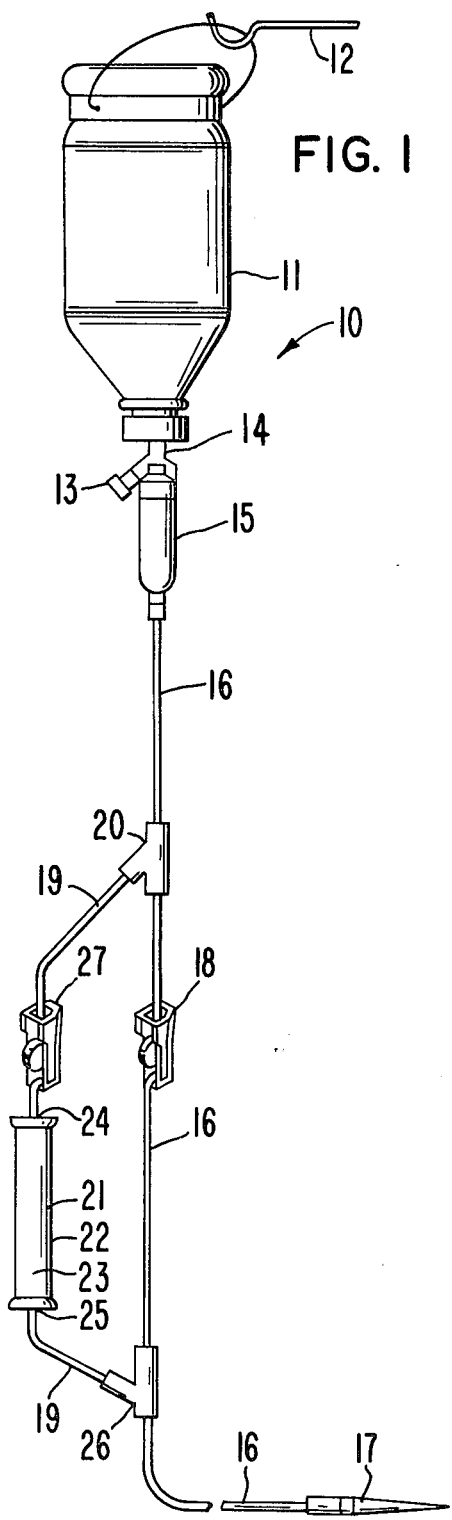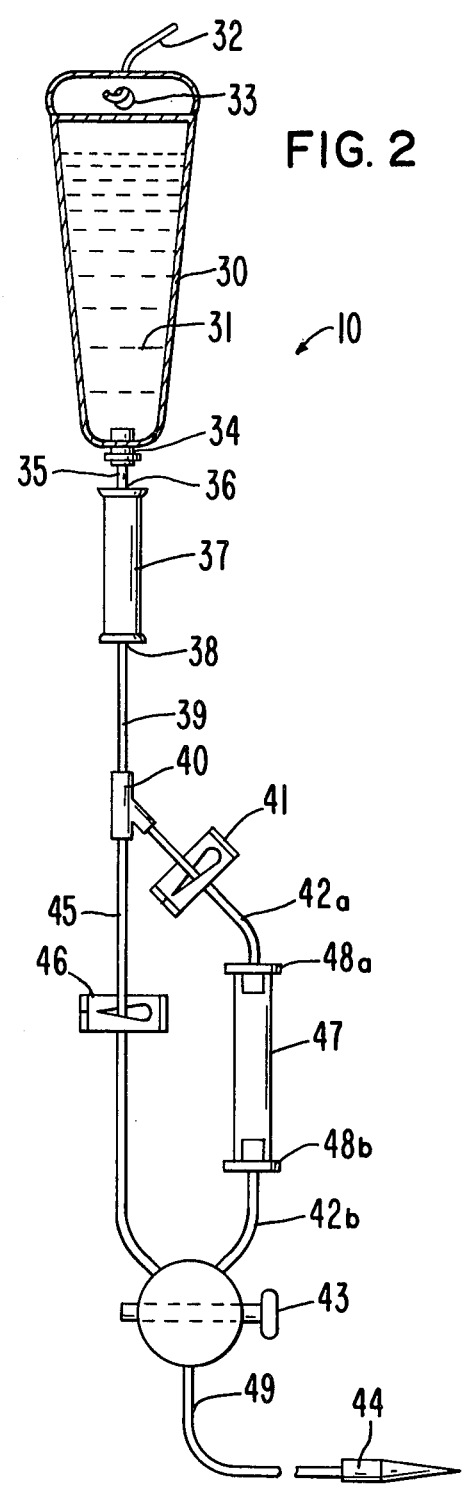

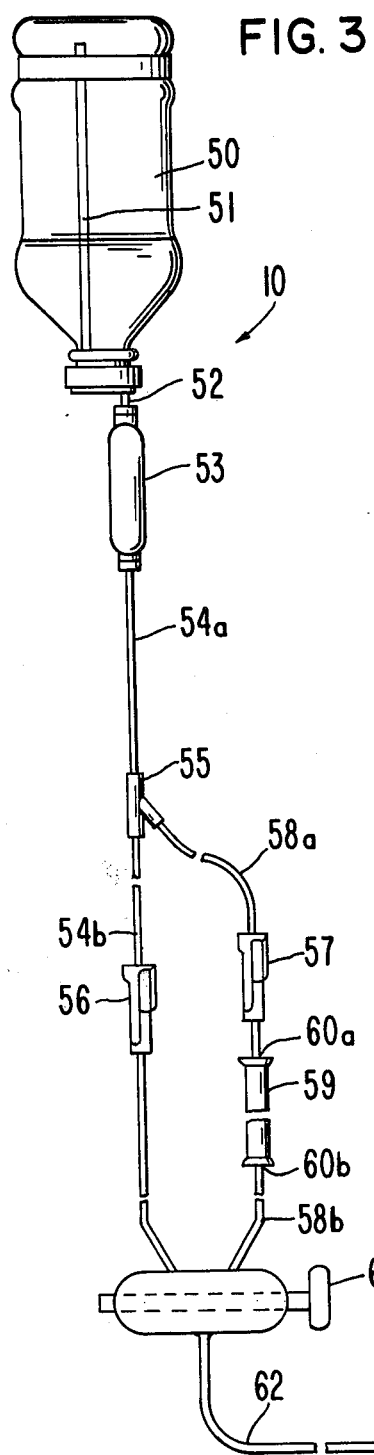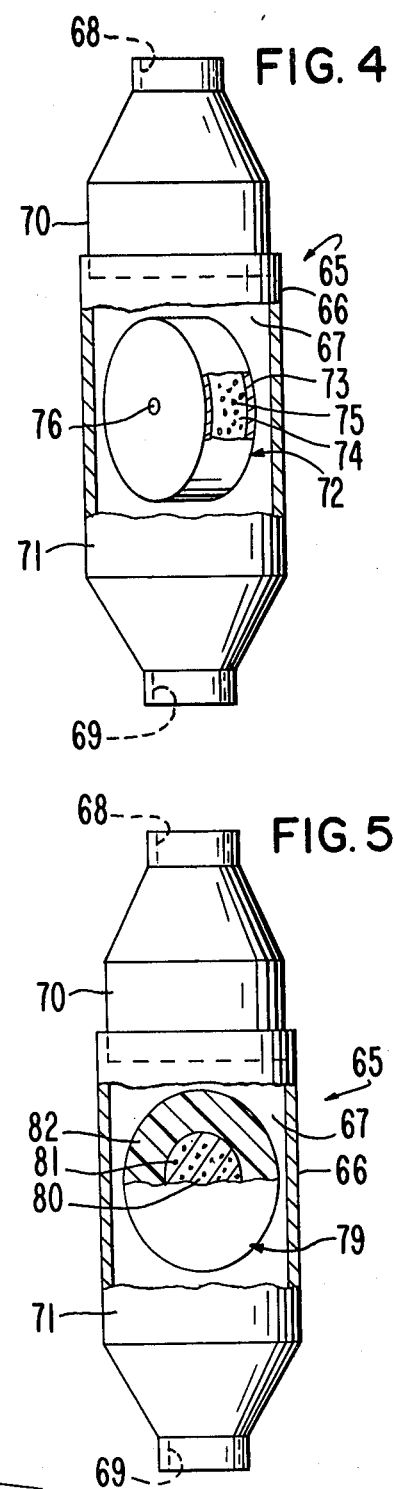

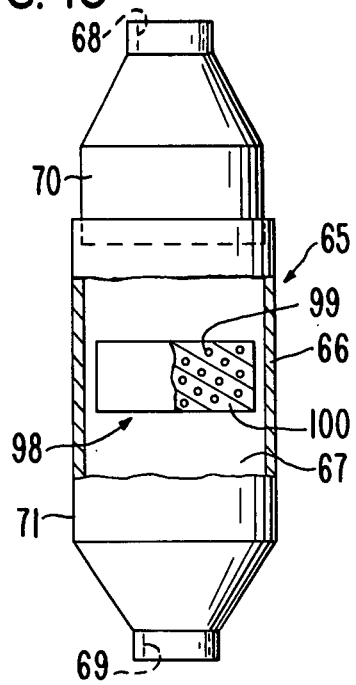
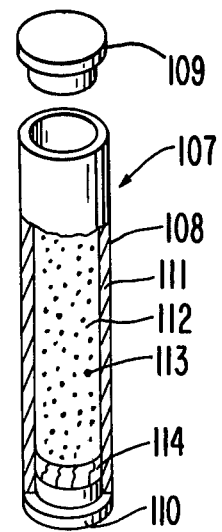
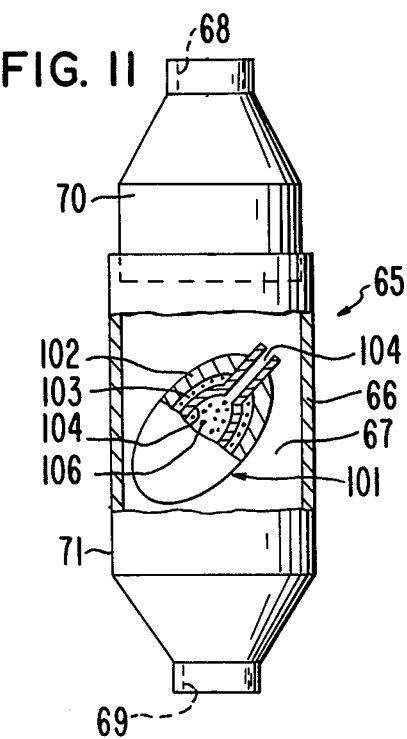
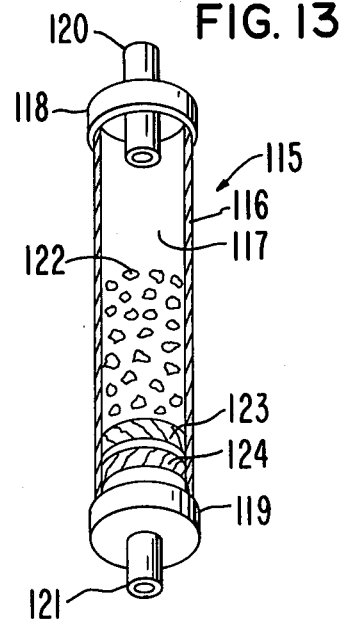

PARENTERAL ADMINISTRATION USING DRUG DELIVERY DEVICE

CROSS-REFERENCE TO COPENDING APPLICATIONS

This application is a continuation of parent application Ser. No. 325,204 filed on Nov. 27, 1981, now U.S. Pat. No. 4,424,056, issued on Jan. 3, 1984.

This application is copending with United States patent application identified as U.S. Ser. No. 325,206 filed Nov. 27, 1981, now U.S. Pat. No. 4,432,756, issued Feb. 21, 1984 and filed currently herewith. These applications are assigned to the ALZA Corporation of Palo Alto, Calif.

FIELD OF THE INVENTION

This invention pertains to a parenteral delivery system comprising an agent formulation chamber containing (1) an agent delivery device, or (2) an agent. The invention relates also to a method of administering parenterally an agent using the parenteral delivery system.

BACKGROUND OF THE INVENTION

The parenteral administration of sterile fluids is an established clinical practice. The fluids are administered usually intravenously, and the practice is used extensively as an integral part of the daily treatment of medical and surgical patients. The fluids administered parenterally usually intravenously include, aqueous solutions of dextrose, sodium chloride and various other electrolytes. The fluids commonly administered intravenously include blood and blood substitutes. Generally, the fluids are administered from a container that is suspended above a patient, with the fluid flowing from the container through an administration set and thence to a catheter or a hypodermic needle placed in a blood vessel, usually a vein of the patient. For intraperitoneal administration of fluids, the administration set is connected to a cannula traversing the abdominal wall of the patient.

The administration of fluids parenterally is a valuable and important component of patient care; moreover, the use of parenteral fluids has in recent years expanded beyond its original role of fluid and electrolyte replacement to include serving as the vehicle for the parenteral administration of beneficial agents, notably those which are desirable to administer by infusion via the intravenous, intra-arterial, intraperitoneal or subcutaneous routes. For example, presently a beneficial agent, such as a drug, is administered intravenously by one of the following procedures: temporarily halting the flow of medical fluid, and intravenously administering the drug to the patient through an injection port in the administration set, followed by resumption of medical fluid into the patient; a drug is added to the fluid in the container, or into a volume control chamber in series with the administration set, and then carried by the flow of fluid to the patient; a drug is introduced into a so-called "piggyback" container, which is subsequently connected via a connector, in tributary fashion, to the primary administration set through which the medical fluid is administered to the patient; or a drug is administered by a pump which, by one of various recognized mechanical pumping actions, establishes flow and this determines the flow of fluid containing the drug into a flow path entering the patient, for example, an indwelling venous catheter.

While these delivery techniques are being used, they have certain disadvantages. For example, the administration of a drug through repeated injections into the administration set is inconvenient and represents each time a potential break in sterility; the use of pumps is expensive and sometimes inconvenient because of their size and weight; the rate of drug delivery to the patient is directly dependent on the flow of fluid with all currently practiced means of drug infusion; because of the relative chemical instability of aqueous solutions of many commonly used parenteral drugs, these procedures often require solubilization of the drug medication by the hospital pharmacist or nurse at a time proximate to its administration; and, while it is current practice to give some drugs by brief infusions, typically of 30 to 120 minutes duration repeated 3 or 4 times a day, they do not provide a means for (a) careful coordination of the procedures for solubilization and administration, (b) careful regulation of the flow of drug solution during each period of infusion to insure that infusion is completed within the recommended time.

In view of this presentation, it is immediately apparent a critical need exists for a dependable and practicable parenteral therapeutic delivery system that overcomes the disadvantages associated with the systems known to the prior art. It is also apparent that a pressing need exists for a parenteral delivery system that can be used clinically for administering parenterally a beneficial agent at a controlled rate and in a beneficially effective amount to a patient according to a preselected program comprising continuous administration, repeated administration, at specified intervals of administration, or as needed administration.

DISCLOSURE OF THE INVENTION

Accordingly, a principal object of this invention is to provide both a novel and useful parenteral delivery system for administering a fluid and a beneficial agent at a controlled rate according to a chosen regimen of administration and in an improved manner for optimizing the care of a warm-blooded animal whose prognosis benefits from parenteral administration.

Another object of the invention is to provide a parenteral delivery system comprising (1) a primary fluid path, and (2) a parallel fluid path comprising a formulation chamber for admitting a beneficial agent into the primary path for optimizing the rate and duration parameters of parenteral administration.

Another object of the invention is to provide a parenteral delivery system comprising (1) a primary fluid path, and (2) a parallel path comprising an agent formulation chamber containing an agent delivery device for delivering an agent at a rate governed by the device into a medical fluid that flows from the primary path into the chamber, and hence through the parallel path into the primary path.

Another object of this invention is to provide a parenteral delivery system comprising (1) a primary fluid path and (2) a parallel path comprising an agent formulation chamber housing a beneficial agent that forms in situ, with fluid that enters the chamber from the primary path, an agent solution that is conveyed back into the primary path for administration to an animal, including a human patient.

Another object of this invention is to provide a delivery system comprising (1) a primary fluid path and (2) a parallel fluid path having a formulation chamber, and which system can be used for improved health care by making available to the practitioner (a) a mechanism for administering a fluid via the primary path, (b) a mechanism for administering a fluid containing a beneficial agent via the parallel path, and (c) a mechanism for controlling the volume and the concentration of agent administered by adjusting the rate through the primary path and by adjusting concomitantly the rate of flow through the parallel path prior to their mixing into a single fluid for its subsequent administration.

Another object of this invention is to provide a parenteral delivery system that comprises a means for automatically constituting an agent formulation in situ by dissolving a given amount of agent in a given volume of fluid that can be administered at any selected time.

Another object of this invention is to provide a parenteral delivery system that makes attainable a program of agent administration adapted to a specific need by furnishing an agent formulation comprising a known volume of fluid containing from a trace to a saturating amount of a beneficial agent that can be administered at any chosen time.

Another object of this invention is to provide a parenteral delivery system comprising a means for administering a known amount of a beneficial agent in a given volume of parenteral fluid.

Another object of this invention is to provide a parenteral delivery system that makes available a regimen of agent administration comprising intervals of agent administration at a specified rate and for a specified duration, alternating with intervals during which no agent is delivered by the system.

Another object of this invention is to provide a parenteral delivery system that makes possible a means for converting a continuously functioning process of agent formulation and release into a method of agent administration that occurs at predetermined periods according to a specified rate and duration of agent administration.

This invention concerns a parenteral delivery system for the administration of a medical fluid containing a beneficial agent to an animal, including a human patient. The system comprises: (1) a primary fluid path consisting of a container of medical fluid and a tube that communicates from the container to an infusion site in the animal; (2) a parallel fluid path having distal ends in fluid communication with the primary path and an agent formulation chamber in the parallel path. The formulation chamber comprises: (a) a wall surrounding a lumen and has a surface that permits communication with the parallel path to let a fluid flow from the container into the formulation chamber; (b) a delivery device containing a beneficial agent that is released into the formulation chamber, or a beneficial agent in the formulation chamber, which agent in either instance forms an agent formulation with fluid that enters the formulation chamber; and (c) an outlet surface that lets agent formulation leave the formulation chamber and enter the parallel path and then into the primary path for administration to the patient. The system additionally comprises a mechanism that can optionally be used for converting a continuously functioning process of agent formulation and release (a) into the parallel flow path so that agent administration into the patient occurs during quantitatively predetermined intervals according to a specified rate and duration of agent infusion, or (b) from the formulation chamber into a regimen of agent administration to the patient characterized by intervals of agent infusion at a specified rate and specified duration alternating with intervals during which no agent reaches the infusion site in the patient.

BRIEF DESCRIPTION OF THE DRAWINGS

In the drawings, which are not drawn to scale but are set forth to illustrate various embodiments of the invention, the Figures are as follows:

FIG. 1 is a perspective view of a parenteral delivery system provided by the invention;

FIG. 2 is a view illustrating another embodiment of the parenteral delivery system;

FIG. 3 is a view of yet another embodiment of the parenteral delivery system;

FIG. 4 is a view of an agent formulation chamber adapted for use in the parenteral delivery system, with the chamber housing an osmotic agent delivery device;

FIG. 5 is a view of an agent formulation chamber containing an agent delivery device comprising a release rate controlling membrane surrounding a reservoir containing a beneficial agent;

FIG. 10 is a view of an agent formulation chamber containing a delivery device comprising depots of agent;

FIG. 11 is a view of a formulation chamber containing a delivery device comprising a housing and a driving member surrounding a flexible container;

FIG. 12 is an opened view of a formulation chamber comprising a beneficial agent and a release rate controlling membrane; and, FIG. 13 is an opened view of an agent formulation chamber comprising a beneficial agent, a release rate controlling membrane and a filter.

In the specification and the drawings, like parts in related Figures are identified by like numbers. The terms appearing earlier in the specification and in the description of the drawings are described hereafter in the disclosure.

MODES FOR CARRYING OUT THE INVENTION

Figure 6:
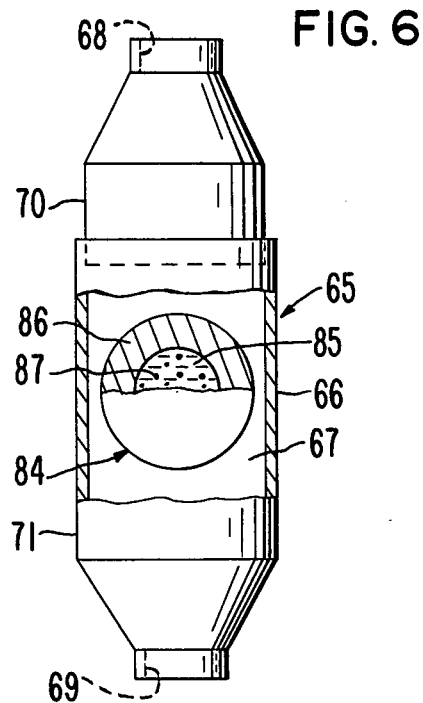
FIG. 6 is a view of a formulation chamber containing a delivery device comprising a release rate controlling membrane surrounding a different reservoir containing a beneficial agent.

FIG. 1 represents a parenteral delivery system provided by the invention and designated by the numeral 10. System 10 of FIG. 1 illustrates a vented-type system that requires air to operate. System 10 comprises a glass container 11, suitably sealed with a rubber stopper and it contains a medical fluid acceptable for parenteral including intravenous administration. Container 11 is supported in delivery position by support 12, and air enters container 11 via air filter 13 connected to container 11 through spike 14 that is hollow and pierces the rubber closure of container 11. The other point of spike 14, not seen, enters a drip chamber 15 and it conveys medical fluid from container 11 into drip chamber 15.

Drip chamber 15 is connected to a primary fluid path 16 formed of a medical grade tubing that conveys medical fluid to needle 17. A roller valve clamp 18 is provided on fluid path 16 for restricting the internal diameter of path 16 for regulating the flow of fluid througn path 16. System 10 of FIG. 1 also comprises a parallel fluid path 19 connected to primary path 16 at branch couplers 20 and 26. Branch couplers 20 and 26 can be made as a Y-type connecting tube for receiving primary path 16 and parallel path 19 for supplying medical fluid from container 11 through primary path 16 into parallel path 19. Parallel path 19 is connected to an agent formulation chamber 21 that is sized and adapted for use in parenteral delivery system 10. Agent formulation chamber 21 is self-contained, self-priming, self-powered and amenable to low cost manufacture. Formulation chamber 21 is lightweight and disposable and it comprises a wall 22 that surrounds and defines an internal lumen or space 23. Chamber 21 has an inlet 24 for receiving parallel path 19 and it has an outlet 25 also adapted for placing chamber 21 in path 19. Chamber 21 is made of glass, plastic or the like, and as illustrated it is made of a transparent material for viewing its structure. Chamber 21 can house a beneficial agent or an agent delivery device.

The agent in chamber 21 can be in any pharmaceutical state that forms an agent formulation with a medical fluid that enters chamber 21, and the use of chamber 21 with an agent therein does not require any reconstitution, or admixture prior to use. An agent formulation formed in chamber 21 leaves the chamber through parallel path 19 and it enters primary path 16 for administration to an animal, including a human patient, through needle 17. Exemplary pharmaceutically acceptable forms that can be used in chamber 21 include solid, crystalline, microcrystalline, particle, pellet, granules, powder, tablet, spray-dried, lypohilized, forms that dissolve or undergo disintegration and dissolution in the presence of a parenteral fluid including intravenous fluids, compressed forms that undergo disintegration and dissolution in the presence of a fluid such as compressed, compressed powders, compressed granules, friable layers of agent, and/or the like. Agent formulation chamber 21 generally will store an amount of agent for executing a prescribed therapeutic or beneficial program. That is, an amount of agent for the preprogrammed, delivery of a therapeutically or a beneficially effective amount of the agent to produce a therapeutic or a beneficial result. Agent formulation chamber 21 generally will have a capacity of from about 10 milliliters to 250 milliliters of fluid or more, and it can house from about 5 milligrams to 20 grams of agent or more. The expression beneficial agent, as used herein, generically denotes any substance that produces a therapeutic or a beneficial result, such as a drug, a carbohydrate, an electrolyte and/or the like. The term fluid or liquid denotes a fluid, or a liquid that can be administered parenterally including intravenously, comprising pharmaceutically acceptable fluids that are also a pharmaceutically acceptable carrier for an agent, such as water, isotonic saline, Ringer's lactate, and the like. The term formulation, and agent formulation as presently used herein, generically indicates the beneficial agent is formulated, mixed, added, dissolved, suspended, solubilized, formulated into a solution, carried and/or the like in or by the fluid in a physical-chemical form acceptable for parenteral including intravenous administration. The flow of medical fluid into formulation chamber 21 can be started, stopped or regulated by clamp 27 that permits tube 19 to remain opened, shut, or it partially obstructs the passage of fluid through tube 19, and correspondingly the flow of agent solution likewise can be governed from chamber 21.

The delivery device housed in formulation chamber 21 releases an agent at a rate controlled by the device. The agent, on its release, is formulated in the chamber with fluid that is a pharmaceutically acceptable carrier for the agent into a parenteral including intravenous administrable agent formulation, such as a drug solution. Devices that can be used for this purpose are those that release an agent by dissolution, diffusion or osmotic mechanism, or by any other physical-chemical mechanism that produces an agent formulation. The amount of agent in a formulation made in chamber 21 can be a trace amount to a saturating amount. The delivery devices, in one presently preferred embodiment are devices that cease releasing agent or shut themselves off in the presence of a saturated agent formulation, that is a saturated solution.

In operation, parenteral delivery system 10 as illustrated in FIG. 1 can be used by a physician, a nurse, or a practitioner in a hospital setting as follows: (1) for administering a medical fluid by adjusting regulator valve 27 to prevent the flow of fluid into formulation chamber 21, thus assuring that fluid will flow through primary path 16 and into skin-piercing means 17; (2) for administering a medical fluid containing a beneficial agent by adjusting regulator valve 18 to prevent the flow of fluid through primary path 16, thereby directing the flow of fluid into parallel path 19 through opened valve 27 and into formulation chamber 21, with agent formulation leaving chamber 21 through tube 19, union 26, tube 16 and into skin-piercing means 17; and (3) for administering an amount of agent in a known volume of fluid arrived at by regulating fluid flow through valve 18 and regulating fluid flow through valve 27 and its accompanying flow through chamber 21, which fluid in both instances mixes into a common fluid at coupling 26 for its subsequent administration to a recipient. The operations provided by this embodiment of the invention makes available continuous and interrupted agent administration, and intervals of agent-free fluid administration.

The performance of a parenteral delivery system used for the purpose of the invention, also can be described mathematically in terms of the physical and chemical functionality of the parenteral system. Generally, parenteral systems encompassed by this invention are those for which $Q_R \leq 0.1 Q_{KVO}$, wherein $Q_{KVO}$ is the flow of fluid required to maintain flow into the veins of an animal in which the flow path terminates, by needle or catheter. This flow is referred to as the "keep vein open", rate $Q_{KVO}$, and it typically is for an adult patient about 10–20 drops per minute, or 0.5–1.0 ml per minute. The symbol $Q_R$ is the maximum rate of fluid flow needed for the parenteral delivery system to deliver a solution at its label rate. Thus, parenteral systems for adult use require less than 0.05–0.1 ml/min to achieve label delivery rate, and show independence of delivery rate from flow at all higher flows are encompassed by this invention. Delivery systems for pediatric use will have a lower absolute limit, but still satisfy the general criterion $Q_R \leq 0.1 Q_{KVO}$.

FIG. 2 illustrates another operative parenteral therapeutic system 10 provided by the invention. System 10 comprises a container 30 formed of a flexible, or a semi-rigid, preferably transparent plastic, such as a non-toxic polyolefin, polyvinyl chloride or the like, and it contains a medical fluid 31 adapted for parenteral, intravenous or other therapy. Medical liquid 31 in container 30 will be typically a sterile solution, such as an aqueous solution of dextrose, electrolytes, or saline. Medical fluid 31 also is a pharmaceutical vehicle for parenteral administration, and it is a pharmaceutical carrier for a drug that is to be administered to a recipient. Container 30, in the embodiment illustrated, is non-vented, the medical fluid is at atmospheric pressure, and the container collapses as it empties of medical fluid 31. Container 30 usually is adapted to be hung neck-down from a hanger 32 by a bib or hole 33 that connects, or is integrally formed as part of container 30. Container 30, at its end distant from its hanging end, that is, at its neck end has an administration port 34 adapted for receiving an administrative set.

The administration set provided by this invention is used to deliver medical fluid 31 and a drug administered by parenteral therapeutic system 10 to a patient. The administration set is sterile, pyrogen-free, and disposable. The administration set comprises the components described hereinafter, and it connects with port 34 of container 30. Port 34 can be a diaphram in container 30, not shown, or port 34 can be an adapter for receiving a hollow connector 35. Connector 35 is made to receive end 36 of drip chamber 37. Drip chamber 37 is used to trap air and it also permits, in cooperation with regulator clamp 46, adjustment of the rate of flow of medical fluid 31 from container 30 as the flow proceeds dropwise. An outlet 38 of drip chamber 37 is connected to one end of a first segment of primary tube 39 having clamp 46 for pinching its internal diameter to regulate flow in cooperation with drip sight chamber 37. The other end of primary tube 39 connects to a Y-type coupler 40 that also receives one end of a parallel tube 42a, and end of a second section of primary tube 45. The other end of tube 45 connects to a valve 43, beyond which tube 49 connects from valve 43 to an adapter needle assembly 44 that is inserted, for example, into the vein of a warm-blooded animal.

Parallel tube 42a is equipped with a clamp 41 for governing the flow of fluid into an agent formulation chamber 47, and another section of parallel tube 42b connects formulation chamber 47 with valve 43. Formulation chamber 47 is made of glass or plastic, and it is preferably transparent. Formulation chamber 47 can have any shape adapted for use in a parenteral therapeutic system, and it is preferably round and its length exceeds its width. The ends of parallel tubes 42a and 42b mate snugly with end caps 48a and 48b of chamber 47. The ends of the parallel tube can fit into caps 48a and 48b, or they can slide over a tube receiving member of caps 48a and 48b to form an air-tight, leak-proof chamber for containing at least one beneficial agent, or a delivery device. Chamber 47 optionally is equipped with a release rate controlling membrane, not shown in FIG. 2, for example a microporous membrane or the like, that governs the rate of release of agent solution from chamber 47. A release rate controlling membrane can rest on a sintered glass support integrally made into the chamber, optionally a membrane can be sealed adhesively to the inside wall of chamber 47, fused thereto, be supported by the wall of the chamber pinched inwardly, rest on a rim in the chamber, or it can be supported or suitably fixed to end cap 48 positioned in chamber 47. A segment of tube 42b conveys agent solution from chamber 47 to valve 43. Valve 43, in a presently preferred embodiment is a two-position valve.

In operation, valve 43 in one position permits the passage of drug solution from chamber 47 to flow into tube 49, while concomitantly stopping flow via tube 45; in its alternate second position, valve 43 stops flow of fluid in tube 42a, 42b, but it allows flow in tube 45. When valve 43 is in its first position, the flow of medical fluid reaches the patient at a rate determined by the setting of regulating clamp 41; when valve 43 is in its second position, the flow of medical fluid reaches the patient at a rate determined by the setting of flow regulating clamp 46. During the intervals of time valve 43 is in its second position, drug formulation proceeds in the presence of fluid in chamber 47 and its release continues from formulation chamber 47 into tube 42b, but it cannot reach the patient, and so it accumulates in chamber 47 and tube 42b. When valve 43 is switched to its first position, accumulated drug formulation solution in chamber 47 and tube 42b enters the patient, the quantity of which is governed by the following expression indicating the delivery of the accumulated amount plus the amount when valve 43 is left in position 1 and $$\int_{t_j}^{t_k} R_1(t)dt + \int_{t}^{t_L} R_2(t)dt$$

wherein $t_j$ equals the time valve 43 is switched from position 1 to position 2; $t_k$ equals the time valve 43 is switched from position 2 to position 1; $t_L$ equals the time valve 43 can be switched from position 1 back to position 2; and $R_1(t)$ equals the rate at which formulation chamber 47 prepares and releases drug in solution; $R_2(t)$ is the rate at which the formulation chamber prepares drug solution during free flow of intravenous fluid. The rate at which agent reaches a patient when valve 43 is switched to position 1, and it is related to the flow regulation imposed by clamp 41, which preferably should be adjusted to allow flow to occur at a rate which insures that all accumulated agent enters the patient. While the above system and its operation were described with a representative manually operated valve, it is to be understood other valve systems are embraced by this invention. For example, electro-mechanical devices that automatically switch back and forth between positions 1 and 2 at preset time intervals are within the scope of this invention.

FIG. 3 illustrates another intravenous system 10 provided by the invention. System 10 comprises in combination a container 50 that is a reservoir of a pharmaceutically acceptable liquid and it has an internal venting tube 51 which allows air to enter container 50 as medical fluid is infused into a patient. Container 50 is closed with a stopper, not shown and it has a hole for venting tube 51. Container 50 is connected through a non-vented hollow spike adaptor 52 to a parenteral delivery system for sending medical fluid from container 50 through system 10 to a patient. Spike 52 is in fluid communication with a drip chamber 53, which as previously described, is made preferably of a see through material, such as a glass or plastic for visibly counting the number of drops that pass through said drip chamber over unit time. Medical fluid leaves drip chamber 3 through a first section of a primary tube 54a that connects to a three-way connector 55, which tubing continues as a second section of primary tubing 54b. The second section of primary tubing 54b passes through a flow regulator clamp 56, that is used for regulating fluid flow from container 50, and for conveying fluid to two-way valve 61, and hence from valve 61 through fluid communicating tube 62 and needle assembly 63 to a recipient. At connector 55 a first section of parallel tube 58a conveys a medical fluid from container 50 to agent formulation chamber 59. Tube 58a passes through a regulator clamp 57 that can be used as an on-off, or volume flow regulator. Agent formulation chamber 59 is as described earlier comprised of a wall formed of a fluid impermeable material that surrounds an internal space for housing a dosage unit amount of a beneficial agent, or a delivery device. Chamber 59 has a known volume and preferably a volumetric scale thereon for indicating the volume of fluid in said chamber. Chamber 59 has an end 60a adapted for receiving incoming tube 58a and fluid from container 50, and it has an end 60b adapted for receiving outgoing tube 58b. Tube 58b conveys fluid carrying the beneficial agent from chamber 59 to valve 61, and thence through fluid communicating tube 62 to needle assembly 63, and to the recipient.

In operation, parenteral delivery system 10 of FIG. 3 is used like parenteral delivery system 10 of FIG. 2. That is, system 10 of FIG. 3 can be used (1) for administering a medical fluid that is free of agent by closing regulator 57, opening regulator 56 and positioning valve 61 to let fluid flow from tube 54b and into tube 62; (2) for administering continuously a medical fluid containing a beneficial agent by closing regulator 56, opening regulator 57 to permit fluid to flow through formulation chamber 59 wherein the agent is added to the fluid, and positioning valve 61 to let fluid flow through tube 58b and into tube 62; and (3) for administering at a selected dosing time a given volume of fluid containing a known amount of agent by (a) permitting fluid to flow through the primary path while setting valve 61 in closed position for the parallel path, (b) permitting a known volume of fluid to enter the formulation chamber, which volume is ascertained by reading the meniscus against the volumetric scale on the chamber, and closing regulator clamp 57 to stop the flow of additional fluid into the formulation chamber, (c) formulating the agent formulation in the chamber by dissolving a given amount of agent present in the chamber, or delivered by a device therein, in the known volume of fluid, which amount of agent in solution is given by the volume times the agent solubility in the fluid dissolved over time, and (d) dosing a recipient with the agent solution whenever desired by positioning valve 61 to let it flow from the formulation chamber.

FIGS. 4 through 13 depict a formulation chamber 65 housing delivery devices or a drug that can be used in the parallel paths of the parenteral delivery system of FIGS. 1 to 3. The formulation chambers described in this specification are the invention disclosed and claimed by Felix Theeuwes in copending patent applications Ser. No. 283,077, filed July 13, 1981 and Ser. No. 289,082 filed July 31, 1981, both now abandoned. Both of these applications are assigned to the ALZA Corporation of Palo Alto, Calif., the assignee of this patent application.

FIGS. 4 through 11 depict the identical formulation chamber 65, housing different delivery devices. The Figures are enlarged for illustrating their components. In these Figures, and turning first to FIG. 4, chamber 65 is seen comprising a wall 66 that has a section removed for viewing its internal space 67. Chamber 65 has an inlet 68 adapted and sized for placing chamber 65 into the parallel path of a parenteral therapy system, and it has an outlet 69 also adapted and sized for placing chamber 65 in the system. Inlet 68 and outlet 69 can be optionally a tube receiving female opening, or any other suitable means adapted for placing chamber 65 in a parenteral system. In chamber 65 of FIGS. 4 through 11, chamber 65 comprises a pair of interfitting houses 70 and 71 for containing a delivery device 72 within lumen 67. The delivery device 72 illustrated in FIG. 4 is an osmotic rate-controlled solid dosage delivery form as described by patentee Felix Theeuwes and Takeru Higuchi in U.S. Pat. No. 3,845,770. The osmotic device 72, seen in opened section, comprises a semipermeable wall 73, such as cellulose acylate, cellulose diacylate, cellulose triacylate, cellulose acetate, cellulose diacetate, cellulose triacelate, that surrounds and forms an agent or drug compartment 74. Compartment 74 contains an agent formulation 75, represented by dots, which formulation exhibits an osmotic pressure gradient across wall 73 or device 72 against fluid in chamber 65. The agent formulation can comprise an agent that exhibits an osmotic pressure gradient, or the agent formulation can comprise an agent mixed with an osmotically effective solute, such as sodium chloride, potassium chloride and the like, that exhibit an osmotic pressure gradient substantially greater than the fluid in chamber 65. A passageway 76 extends through semipermeable wall 73 and communicates with compartment 74 and the exterior of device 72. In operation, fluid enters into chamber 65 and is imbibed through the semipermeable wall of device 72 into compartment 74 in a tendency towards osmotic equilibrium at a rate determined by the permeability of the wall and the osmotic pressure gradient across the wall, thereby producing a solution in compartment 74 that is dispensed through passageway 76 at a rate controlled by device 72 over a prolonged period of time. The delivery of agent formulation from device 72 for homogenously blending with fluid in chamber 65, is controlled in this embodiment by device 72 and it is essentially independent of the rate of fluid flow through chamber 65. Device 72 maintains its physical and chemical integrity throughout its releasing history.

FIG. 5 depicts formulation chamber 65, in opened section, containing another device 79 for delivering an agent into a parenteral delivery system including an intravenously acceptable fluid that enters chamber 65. Device 79 is illustrated in opened-section and it comprises an inner mass transfer conductor 80, illustrated as a solid core and formed of a polymeric material such as cured polydimethylsiloxane with agent 81 dispersed therethrough. Surrounding mass transfer conductor 80 is a release rate controlling membrane 82, preferably formed of a polymeric material, such as polyurethane. Both conductor 80 and membrane 82 are permeable to the passage of agent 81 by diffusion, that is, agent can dissolve in and diffuse through conductor 80 and membrane 82. However, the permeability of conductor 80 is greater than that of membrane 82, and membrane 82 thus acts as the rate controlling member for agent release from device 79. Device 79 maintains its physical and chemical integrity throughout the period of drug delivery. Delivery device 79 is disclosed in U.S. Pat. No. 3,845,480.

FIG. 6 illustrated the formulation chamber 65, with a section of its wall 66 removed, housing delivery device 84 for delivering an agent at a rate controlled by device 84 into a fluid that enters chamber 65. Device 84 is seen in opened-section and it comprises a reservoir 85 formed of a liquid mass transfer conductor, such as a medical oil carrier, permeable to the passage of agent 87, such as the drug phenobarbital. Reservoir 85 is surrounded by a wall 86 formed of a release rate controlling material permeable to the passage of agent 87, such as a polyolefin. The rate of passage of agent 87 is lower through membrane 86 than the rate of passage through conductor 85, so that agent released by wall 86 is the agent release rate controlling step for releasing agent 87 from device 84. Device 84 maintains its physical and chemical integrity throughout its release history. Delivery device 84 is disclosed in U.S. Pat. No. 3,993,073, which patent is incorporated herein by reference.

Figure 7:
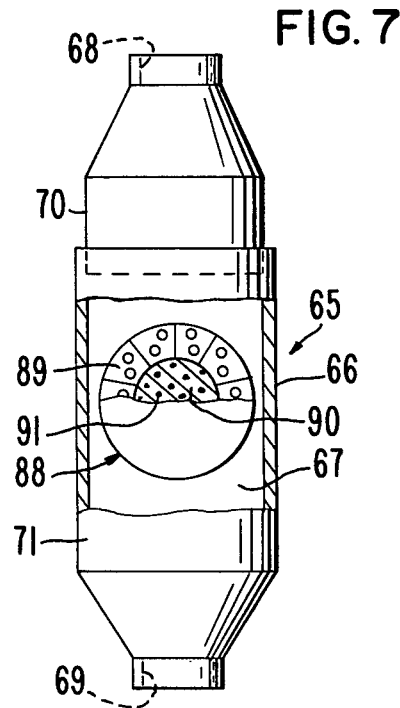
FIG. 7 is a view of an agent formulation chamber containing an agent delivery device comprising a microporous membrane surrounding a reservoir containing a beneficial agent.

FIG. 7 illustrates formulation chamber 65, with part of its wall removed, housing another device 88 for deliverying an agent into a liquid that enters chamber 65 for forming a parenteral agent including an intravenously acceptable agent solution. Device 88 is seen in opened-section and it comprises a wall 89 surrounding a reservoir 90 containing agent 91. The reservoir is formed of a solid carrier permeable to the passage of agent, such as cured polydimethylsiloxane containing diazepam. Wall 89 is formed of a microporous material, for example a microporous polymer made by coprecipitation of a polycation and a polyanion. The release of agent 91 is controlled by device 88, which device 88 maintains its physical and chemical integrity during the period of time it is in chamber 65. Device 88 is disclosed in U.S. Pat. No. 3,993,072, which patent is incorporated herein by reference.

Figure 8:
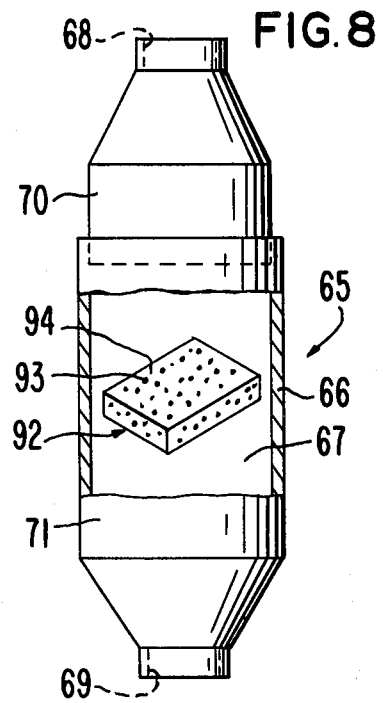
FIG. 8 is a view of an agent formulation chamber containing a delivery device comprising a matrix containing a beneficial agent.

FIG. 8 is a view of formulation chamber 65 having part of its housing removed and it contains device 92 for delivering an agent into a medical fluid that enters chamber 65 for forming in situ a parenteral or an intravenously acceptable agent formulation solution. Device 92 comprises a matrix 94 containing agent 93 distributed therein. Matrix 94 is formed from a polymeric material that is non-erodible and it is permeable to the passage of agent by diffusion for releasing agent over time, or it undergoes relaxation and releases agent 93 over time. The matrix can possess any shape such as rod, disc and the like that fits into chamber 65. The polymers include polyolefins such as polyethylene containing an agent such as muscle relaxants and the like. Materials useful for manufacturing the devices are disclosed in U.S. Pat. No. 3,921,636.

Figure 9:
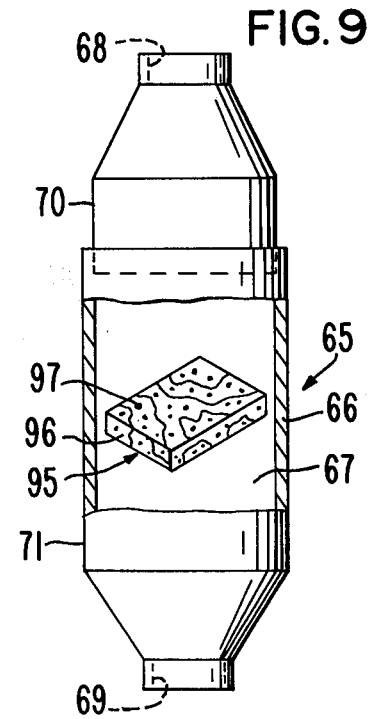
FIG. 9 is a view of an agent formulation chamber containing a delivery device comprising a microporous matrix containing an agent.

FIG. 9 is a view of formulation chamber 65, in opened view, housing device 95 for delivering a beneficial agent into a fluid that enters chamber 65. Device 95 is formed of a microporous polymeric matrix 96 containing agent 97 distributed therethrough. Matrix 96 is formed of a non-toxic, inert polymer, that is non-erodible and has a plurality of micropores for releasing agent 97 at a controlled rate to fluid entering chamber 65. Microporous materials useful for the present purpose are disclosed in U.S. Pat. Nos. 3,797,494 and 3,948,254.

FIG. 10 illustrates formulation chamber 65, in opened view, housing device 98 for delivering a beneficial agent into a medical fluid that enters chamber 65. Device 98 is seen in opened section and it comprises depots of medication solute 99 dispersed in and surrounded substantially individually by a polymer wall 100 that is impermeable to the passage of medication solute and permeable to the passage of fluid that enters chamber 65. Medication solute 99 is released at a controlled rate by fluid from chamber 65 being imbibed through polymer 100 and into depots 98 to dissolve the solute and generate a hydrostatic pressure in the depots, which pressure is applied against the wall of the depot thereby forming apertures that release the medication at a controlled rate over time. Polymer 100 is non-erodible, and device 98 can be shaped as a matrix, rod, a disc, or like shapes. Procedures and materials useful for manufacturing osmotic bursting delivery systems are described in U.S. Pat. No. 4,177,256.

FIG. 11 illustrates formulation chamber 65, in opened view, containing device 101 useful for delivering a drug into a medically acceptable fluid passing through chamber 65. Device 101 is seen in opened view and it comprises an exterior wall 102 formed of a semi-permeable polymer permeable to fluid and substantially impermeable to the passage of drugs and solutes. A layer 103 of an osmotically effective solute, for example sodium chloride, is deposited on the inner surface of wall 102. Solute layer surrounds an inner container 104 formed of a flexible material that is impermeable to solute and drug. Container 104 has a passageway 105 for delivering a drug 106 into a fluid in chamber 65. Device 101 dispenses drug by fluid permeating from chamber 65 through wall 102 to continuously dissolve solute 103 in a tendency towards osmotic equilibrium, thereby continuously increasing the volume between wall 102 and container 104. This increase causes container 104 to continuously collapse and dispense drug 106 from device 101 at a controlled rate through passageway 104 to fluid passing through chamber 65. Osmotically powered agent dispensing devices are disclosed in U.S. Pat. Nos. 3,760,984 and 3,995,631.

The delivery devices described in FIGS. 4 through 11 can contain various amounts of an agent, for example, from about 1 milligram to 20 grams, or more. The devices can release an agent at a rate of 10 nanograms per hour up to 3 grams per hour into chamber 65 for forming an agent solution with the medical fluid that enters chamber 65. The formulation chamber can optionally be considered as a cartridge, since they can be used in the parallel path once or replaced many times. That is, the cartridge can be removed after all the agent is delivered, or the cartridge can be replaced repeatedly each time after the device has delivered its agent. Thus, this mode of the invention can lead to intermediate or continuous therapy, in addition to the operations described in FIGS. 1 to 3.

FIG. 12 depicts another formulation chamber 107 that can be used in a parenteral delivery system as seen in FIGS. 1 to 3. FIG. 12 illustrates formulation chamber 107 that is light wieght, disposable and indicated for use for patients requiring parenteral administration of a drug solution. In FIG. 12, chamber 107 comprises a body 108 of tube shape, and it has a pair of caps 109 and 110 that fit into body 108 for forming a closed chamber 107 for containing a fluid that enters chamber 107 and drug 113. Caps 109 and 110 are preferably made of self-sealing rubber through which a needle or a hollow spike can be inserted, or of rubber with a predrilled hole covered by a latex disc through which communication can be made with the inside of chamber 107. Chamber 107 comprises wall 111 with a section removed for depicting internal lumen 112. Chamber 107 contains drug 113 that is soluble in parenterally acceptable fluids that enter chamber 107, and in a presently preferred embodiment a film 114 formed of a material operable for controlling the release of drug 113 in solution from chamber 107. Film 114 is in a preferred embodiment formed of a release rate controlling polymer, such as a microporous polymer, like a polycarbonate, a semipermeable polymer like cellulose acetate, or a diffusional polymer like ethylene-vinyl acetate copolymer. The polymeric film according to the practice of the invention is used for governing the rate of drug solution release from chamber 107. Chamber 107 is illustrated with a film at its exit, and optionally it can have a film at its inlet.

FIG. 13 illustrates a formulation chamber 115 that can be used in the therapeutic systems described in FIGS. 1 to 3. Chamber 115 comprises a wall 116 that surrounds and defines an internal lumen 117. A section of wall 116 is removed for this purpose. Chamber 115 comprises a pair of closures 118 and 119 that fit over wall 116 for forming a closed chamber 115. The closures 118 and 119 each have a hollow member 120 and 121 that are preferably round for receiving a tube that can slide into, or slide over receiving members 120 and 121, thereby permitting chamber 115 to establish fluid communication with the parenteral therapeutic system. FIG. 13 further illustrates agent as 122 in particle form, a release rate controlling polymeric film 123 and a filter 124. Filter 124 is a conventional filter with a pore size of 0.1 micron to 5 micron, and more preferably 0.22 micron or 0.45 micron, for removing bacteria and unwanted matter from a flowing solution.

The parenteral delivery system comprising the primary path and the parallel path with the agent formulation chamber in the parallel path can be used for the administration of many beneficial agents especially where it is desirable to administer by infusion, and more particularly via the intravenous, intra-arterial, intraperitoneal or subcutaneous routes. For example, the delivery system can be used in one presently preferred embodiment, in intravenous fluid replacement, such as administering plasma or saline and simultaneously or intermittently administering a therapeutically effective amount of drug therewith; in another embodiment as a method in intravenous electrolyte-balance replacement, such as supplying sodium, potassium or chloride ions with drug administered therewith to a patient in need of electrolyte restoration and an intravenous drug; and in a method of intravenous nutrition, such as supplying dextrose and concomitantly administering or periodically administering a parenterally administrable drug to a patient in need of such therapies.

The novel and useful invention provides a system and method for obtaining the precise control of agent administration to a recipient. While there has been described and pointed out features of the invention as applied to presently preferred embodiments, those skilled in the art will appreciate that various modifications, changes, additions and omissions in the invention illustrated and described can be made without departing from the spirit on the invention.

We claim:

1. An administration set for use with a parenteral therapeutic system, the administration set comprising:
   (a) a primary tube for the flow of a medical fluid therethrough;
   (b) a parallel tube in fluid communication with the primary tube for the flow of medical fluid therethrough; and,
   (c) a drug formulation chamber in the parallel tube, the chamber comprising;
      (1) a wall surrounding a space;
      (2) an inlet in the wall that communicates with the parallel tube for receiving fluid into the chamber;
      (3) a drug delivery device in the chamber, said device comprising a wall formed of a microporous material that substantially surrounds a solid reservoir containing a dosage unit amount of a beneficial drug that forms on its release from the device a drug formulation with fluid that enters the chamber and wherein, when the administration set is in operation and administering drug to a recipient, a beneficially effective amount of the drug is administered by the combined operations of the device releasing drug and the rate of fluid flow through the chamber; and,
      (4) an outlet in the wall for the flow of fluid containing drug from the chamber.

2. An administration set for use with a parenteral therapeutic system, the administration set comprising:
   (a) a primary tube for the flow of a medical fluid therethrough;
   (b) a parallel tube in fluid communication with the primary tube for the flow of the medical fluid therethrough; and,
   (c) a drug formulation chamber connected to the parallel tube, the chamber comprising:
      (1) a wall surrounding a lumen;
      (2) an inlet in the wall that communicates with the parallel tube for receiving a fluid that flows into the chamber;
      (3) a drug delivery device in the chamber, the device comprising a matrix formed of a microporous material containing a dosage amount of a beneficial drug that forms on its release from the device a drug formulation with fluid that enters the chamber and wherein, when the administration set is in operation and administering drug to a recipient, a beneficially effective amount of the drug is administered by the combined operations of the device releasing drug and the rate of fluid flow through the chamber; and,
      (4) an outlet in wall for the flow of fluid containing drug from the chamber.

* * * * *